(12) United States Patent
Bujac et al.

(10) Patent No.: US 6,194,621 B1
(45) Date of Patent: *Feb. 27, 2001

(54) PRODUCTION OF DIFLUOROMETHANE

(75) Inventors: Paul David Bernard Bujac, Tarporley; Jane Lesley Butcher, Runcorn, both of (GB)

(73) Assignee: Imperial Chemical Industries, PLC, London (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/663,038
(22) PCT Filed: Dec. 14, 1994
(86) PCT No.: PCT/GB94/02734
  § 371 Date: Jun. 11, 1996
  § 102(e) Date: Jun. 11, 1996
(87) PCT Pub. No.: WO95/17364
  PCT Pub. Date: Jun. 29, 1995

(30) Foreign Application Priority Data

Dec. 23, 1993 (GB) .................................... 9326233

(51) Int. Cl.$^7$ ...................................................... C07C 19/08
(52) U.S. Cl. ............................................ 570/134; 570/169
(58) Field of Search ...................................... 570/169, 134

(56) References Cited

U.S. PATENT DOCUMENTS 5,495,056 * 2/1996 Burgess ................................. 570/142

FOREIGN PATENT DOCUMENTS

WO 93/25509 * 12/1993 (WO) ............................ C07C/17/00

OTHER PUBLICATIONS

The patent WO 93/25509 is prior art cited by the PCT search report and present in application, Dec. 23, 1993.*

* cited by examiner

Primary Examiner—Jean F. Vollano
(74) Attorney, Agent, or Firm—Cook, Alex, McFarron, Manzo, Cummings & Mehler, Ltd.

(57) ABSTRACT

A process for the production of difluoromethane which comprises contacting bis(fluoromethyl)ether in the liquid phase with boron trifluoride under conditions such that the molar ratio of boron trifluoride to bis(fluoromethyl) ether is at least 0.5:1.

12 Claims, No Drawings

PRODUCTION OF DIFLUOROMETHANE

This application is the national phase of PCT/GB94/02734 filed Dec. 14, 1994, now WO95/17364.

This invention relates to a process for the production of difluoromethane from bis(fluoromethyl)ether, $CH_2F$—O—$CH_2F$.

Several methods for the production of difluoromethane are known but many of these methods involve the use of chlorine-containing starting materials, for example chlorodifluoromethane and dichloromethane, and the production of chlorine-containing by-products, for example chlorofluoromethane and fluorodichloromethane.

A chlorine-free process for the production of difluoromethane is also known. In U.S. Pat. No. 3,377,394, there is disclosed a process for the production of difluoromethane and methyl fluoride by contacting formaldehyde with hydrogen fluoride at an elevated temperature in the range from about 100° C. to about 650° C. in the presence of a fluorine-containing inorganic acid, a metal fluoride, a metal oxide or a metal chromite. However, the highest yield of difluoromethane reported from this reaction is 4.2%, the major product being methyl fluoride.

Recently, a process for the production of difluoromethane has been disclosed in published European Patent Application No. 0 518 506 in which bis(fluoromethyl)ether is heated in the vapour phase to elevated temperature. It is also disclosed in this document that bis(fluoromethyl)ether may itself be produced by contacting formaldehyde with hydrogen fluoride and separating the bis(fluoromethyl)ether from the by-product water produced, thus providing a two-step process for the production of difluoromethane in which formaldehyde and hydrogen fluoride are contacted to produce bis(fluoromethyl)ether and water, the bis(fluoromethyl)ether is separated from unreacted starting material and by-product water and the bis(fluoromethyl)ether is then heated to elevated temperature in the vapour phase.

Further, in our co-pending International Application No. GB93/01244 it is disclosed that difluoromethane may be produced from bis(fluoromethyl)ether by contacting bis(fluoromethyl)ether with a Lewis acid in the liquid phase.

We have now found that difluoromethane may be produced from bis(fluoromethyl)ether in the liquid phase in substantially higher yields and selectivities than have previously been described.

According to the present invention there is provided a process for the production of difluoromethane which comprises contacting bis(fluoromethyl)ether in the liquid phase with boron trifluoride under conditions, for example of temperature and pressure, such that the molar ratio of boron trifluoride to bis(fluoromethyl)ether in the liquid phase is at least 0.05:1.

Preferably the molar ratio of boron trifluoride to bis(fluoromethyl)ether is at least 0.08:1, more preferably at least 0.1:1 and especially at least 0.5:1. It is generally economically undesirable to employ a molar ratio of boron trifluoride to bis(fluoromethyl)ether greater than 5:1, and the molar ratio of boron trifluoride to bis(fluoromethyl)ether will generally not be higher than 3:1. We especially prefer to employ a molar ratio of boron trifluoride to bis(fluoromethyl)ether in the range from about 0.5:1 to about 3:1.

The process may be operated so that, based upon the amount of bis(fluoromethyl)ether charged to the vessel, difluoromethane is produced with a yield of at least 50%. Yields of difluoromethane greater than 90% with difluoromethane selectivities greater than 95% have been achieved in practice.

The process is effected under conditions, in particular conditions of temperature and pressure, such that the bis(fluoromethyl)ether is in the liquid phase and preferably under conditions whereby the volatile difluoromethane product distils from the vessel in which the reaction is effected. Furthermore, we prefer that sufficient boron trifluoride is employed and the conditions of temperature and pressure are such that the molar ratio of boron trifluoride to bis(fluoromethyl)ether in the liquid phase is within the aforementioned ranges.

We have found that temperatures below 200° C. tend to favour the selective production of difluoromethane. Preferably the temperature is in the range from about 0° C. to about 180° C., more preferably in the range from about 0° C. to about 150° C. and especially in the range from about 10° C. to about 120° C.

The process may be conducted at atmospheric, subatmospheric or superatmospheric pressure although superatmospheric pressures, say up to 40 barg are preferably employed. In particular we prefer to employ superatmospheric pressures in the range from about 2 barg to about 20 barg. Where the reaction is effected in pressure equipment, for example an autoclave, autogenous pressure is conveniently employed.

The reaction may be conducted in suitable pressure equipment such as an autoclave or in a liquid phase reaction vessel.

The process may be operated as a batch process but is preferably operated as a continuous process in which bis(fluoromethyl)ether and boron trifluoride are continuously fed to the reaction vessel and the volatile products are continuously withdrawn from the vessel.

The process may be conducted in the presence or absence of hydrogen fluoride. Where hydrogen fluoride is employed, the amount of hydrogen fluoride may vary within a wide range, for example in a molar ratio to bis(fluoromethyl)ether in the range from about 0.1:1 to about 20:1.

Any liquid phase complexed or dissolved boron trifluoride may be drained from the vessel and the boron trifluoride may be recovered from the complex, for example as described in U.S. Pat. No. 3,329,585, and recycled. Furthermore, other steps may be taken, as desired, to recover unreacted starting materials, for example formaldehyde, and by-product organic material.

Difluoromethane may be separated from other volatile products of the reaction by conventional techniques, for example distillation.

The bis(fluoromethyl)ether starting material for the process may itself be prepared by the reaction of formaldehyde with hydrogen fluoride as described for example in our European Patent Application No. 518 506 and our International Patent Applications Nos. WO 93/10070 and WO 93/22265, the contents of which are incorporated herein by reference in so far as they relate to the production of bis(fluoromethyl)ether. In particular, the bis(fluoromethyl)ether for the process of the invention will contain less than an equimolar amount of water relative to bis(fluoromethyl)ether. We generally prefer that the bis(fluoromethyl)ether employed in the process contains less than 5% by weight water, and especially less than 2% by weight water. We have achieved high selectivities to difluoromethane where the bis(fluoromethyl)ether employed contains from about 0.01% by weight water to about 1% by weight water.

Whilst the invention is in no way limited by theory, it is known that boron trifluoride has a strong affinity for water, and we believe that boron trifluoride will first complex with any water present so that only the boron trifluoride which is available after all the water present in the reaction vessel has been complexed (i.e. "free" boron trifluoride) can take part in the bis(fluoromethyl)ether reaction. Consequently we prefer that sufficient boron trifluoride is employed so that the molar ratio of free boron trifluoride (i.e. moles of boron trifluoride employed—moles of water present in the reaction vessel):bis(fluoromethyl)ether is at least 0.05:1, preferably 0.08:1, more preferably 0.1:1 and especially 0.5:1.

According to a preferred embodiment of the invention there is provided a process for the production of difluoromethane which comprises the steps (a) contacting formaldehyde with hydrogen fluoride to form bis(fluoromethyl) ether and water, (b) (physically) separating at least a part of the water from the bis(fluoromethyl)ether and (c) contacting the bis(fluoromethyl)ether in the liquid phase with boron trifluoride under conditions of temperature and pressure such that the molar ratio of boron trifluoride to bis (fluoromethyl)ether in the liquid phase is at least 0.05:1.

Steps (a) and (b) are preferably performed together as described in International Patent Applications Nos. WO 93/10070 and WO 93/22265, and especially as described in No WO 93/10070.

The invention is illustrated but not limited by the following examples.

EXAMPLE 1

Runs 1 to 4

In each run about 20 g of bis(fluoromethyl)ether (BFME) and sufficient $BF_3$ to give the molar ratio of bis (fluoromethyl)ether to $BF_3$ detailed for each run in Table 1, were charged to a 70 ml Hastelloy autoclave at room temperature. The autoclave was sealed and heated to a temperature and for a period of time detailed for each run in Table 1. The maximum pressure observed during each run was 40 bar. After the period of time detailed for each run in Table 1, the volatile products were distilled from the autoclave and analysed by Gas Chromatography. The results are shown in Table 1, in which % yields of difluoromethane are based upon the moles of bis(fluoromethyl)ether consumed and % difluoromethane selectivity is based upon the number of moles of difluoromethane per total number of moles of carbon in the vapour.

TABLE 1

| | | | | $CH_2F_2$ | |
|---|---|---|---|---|---|
| RUN No. | $BF_3$:BFME Mole Ratio | TEMP °C. | TIME Hours | YIELD % | SELECTIVITY % |
| 1 | 0.05 | 50 | 17 | 0.9 | 16.4 |
| 2 | 0.92 | 62 | 1 | 41 | 91.2 |

TABLE 1-continued

| | | | | $CH_2F_2$ | |
|---|---|---|---|---|---|
| RUN No. | $BF_3$:BFME Mole Ratio | TEMP °C. | TIME Hours | YIELD % | SELECTIVITY % |
| 3 | 1 | 37 | 17 | 92.42 | 93.3 |
| 4 | 1.13 | 38 | 2 | 58.4 | 97.2 |

EXAMPLE 2

Runs 5 to 10

The procedure of example 1 was repeated except that bis(fluoromethyl)ether was charged to the autoclave as a 50:50 wt % mixture with hydrogen fluoride. The results are shown in Table 2, in which % yields of difluoromethane are based upon the moles of bis(fluoromethyl)ether consumed.

TABLE 2

| | | | | $CH_2F_2$ | |
|---|---|---|---|---|---|
| RUN No. | $BF_3$:BFME Mole Ratio | TEMP °C. | TIME Hours | YIELD % | SELECTIVITY % |
| 5 | 0.08 | 50 | 48 | 11.8 | 23 |
| 6 | 0.1 | 50 | 17 | 55.6 | 69.1 |
| 7 | 0.35 | 75 | 4 | 26.2 | 50.73 |
| 8 | 0.67 | 50 | 16 | 78.8 | 93.2 |
| 9 | 1.37 | 56 | 2 | 73.4 | 96.3 |
| 10 | 2 | 38 | 1 | 46.6 | 97.8 |

EXAMPLE 3

Runs 11 to 19

A quantity of BFME/HF (~100 g) is initially charged to a 500 ml CSTR (Continuous Stirred tank Reactor) and heated to the required reaction temperature. BFME/HF and BF3 are then simultaneously fed at such a rate to achieve the desired residence time. Prior to entering the reactor, the $BF_3$ and BFME/HF streams are mixed in a cooled gas absorber. A Pressure regulating valve (GO valve) is employed to regulate and set the desired reaction pressure. A continuous vapour off-take allows sampling of the reactor gas. This vapour passes through a scrubbing system and is not collected. An overflow pipe situated in the bottom of the reactor allows the continuous off-take of liquid into a metal collection vessel (a whitey bomb) which acts as a residual collection vessel. In this way continuous operation of the process is simulated. The results are shown in Table 3 in which $CH_2F_2$% yields are based upon the number of moles of bis(fluoromethyl)ether consumed rather than the number of moles of carbon consumed and a value >100% is indicative of co-produced formaldehyde reacting on to BFME and then $CH_2F_2$.

TABLE 3

| RUN No. | TEMP/ °C. | Pressure/ barg | HF:BFME Ratio | BF3:BFME Ratio | Residence Time/min | $CH_2F_2$ Yield % | $CH_2F_2$ Selectivity % | BFME Conversion % |
|---|---|---|---|---|---|---|---|---|
| 11 | 90 | 3 | 10.8:1 | 0.3:1 | 19.8 | 85.8 | 88.4 | 42.5 |
| 12 | 90 | 3 | 10.8:1 | 1.7:1 | 134 | 119 | 56.6 | 87.9 |
| 13 | 30 | 3.3 | 10.8:1 | 1.1:1 | 20.6 | 37.8 | 93 | 56.1 |
| 14 | 30 | 13 | 10.8:1 | 0.31:1 | 21.2 | 37.2 | 95 | 65.8 |
| 15 | 30 | 2.7 | 10.8:1 | 0.37:1 | 144 | 131.6 | 98.5 | 49.8 |
| 16 | 30 | 9.6 | 10.8:1 | 1.5:1 | 145 | 125.6 | 97 | 91.1 |
| 17 | 62 | 7.4 | 7.1:1 | 1.3:1 | 89 | 117.4 | 96.7 | 92.5 |
| 18 | 30 | 3 | 2.9 | 1.7:1 | 118 | 87.2 | 96 | 80.6 |
| 19 | 90 | 8.5 | 2.97 | 0.38 | 119 | 62 | 78 | 78.5 |

What is claimed is:

1. A process for the production of difluoromethane which comprises contacting bis(fluoromethyl)ether in the liquid phase with boron trifluoride under conditions such that the molar ratio of boron trifluoride to bis(fluoromethyl)ether in the liquid phase is at least 0.5:1.

2. A process as claimed in claim 1 in which the molar ratio of boron trifluoride to bis(fluoromethyl)ether is not greater than 5:1.

3. A process as claimed in claim 1 in which the process is effected under conditions such that the bis(fluoromethyl) ether is in the liquid phase and difluoromethane product distills from the vessel in which the reaction is carried out.

4. A process as claimed in claim 3 in which the temperature is in the range from about 0° C. to about 180° C.

5. A process as claimed in claim 3 in which the temperature is in the range from about 0° C. to about 120° C.

6. A process as claimed in claim 1 in which the process is carried out in the presence of hydrogen fluoride.

7. A process as claimed in claim 1 wherein the process is carried out in the presence of less than 5% by weight water based upon the amount of bis(fluoromethyl)ether.

8. A process as claimed in claim 1 wherein the process is effected in the presence of less than 2% by weight water based upon the amount of bis(fluoromethyl)ether.

9. A process for the production of difluoromethane which comprises the steps of:

A) producing bis(fluoromethyl)ether by contacting formaldehyde with hydrogen fluoride;

B) separating at least a part of the by-product water from the bis(fluoromethyl)ether; and C) contacting the bis(fluoromethyl)ether from Step B in the liquid phase with boron trifluoride tinder conditions such that the molar ratio of boron trifluoride to bis (fluoromethyl)ether is at least 0.5:1.

10. A process as claimed in claim 6 wherein the hydrogen fluoride is present in a molar ratio to bis(fluoromethyl)ether in the range from about 0.1:1 to about 10:1.

11. A process as claimed in claim 1 in which the molar ratio of boron trifluoride to bis(fluoromethyl)ether ranges from 0.5:1 to about 3:1.

12. A process as claimed in claim 9 in which the molar ratio of boron trifluoride to bis(fluoromethyl)ether ranges from 0.5:1 to about 3:1.

* * * * *